United States Patent [19]

Mimasu et al.

[11] Patent Number: 4,681,757
[45] Date of Patent: Jul. 21, 1987

[54] DEODORANT COMPOSITIONS CONTAINING PERSIMMON JUICE AS ACTIVE INGREDIENT

[75] Inventors: Takeo Mimasu, Kyoto; Kuniyoshi Torii, Nishinomiya, both of Japan

[73] Assignee: Rilis Kagaku Kogyo Kabushiki Kaisha, Osaka, Japan

[21] Appl. No.: 783,021

[22] Filed: Oct. 2, 1985

[30] Foreign Application Priority Data

Oct. 8, 1984 [JP] Japan ................................ 59-210211

[51] Int. Cl.⁴ ..................... A61K 7/035; A61K 7/032; A61K 9/10; A61K 31/74
[52] U.S. Cl. ............................... 424/47; 424/DIG. 5; 424/65; 424/69; 424/76; 424/78; 514/783
[58] Field of Search ....................... 424/69, 76, 47, 65, 424/78, DIG. 5; 514/783

[56] References Cited

U.S. PATENT DOCUMENTS

| 1,545,931 | 7/1925 | Weeks ................................... 424/65 |
| 3,080,295 | 3/1963 | Goorley ................................ 424/65 |
| 4,501,730 | 2/1985 | Torii et al. ........................... 424/76 |

FOREIGN PATENT DOCUMENTS

| 0077047 | 4/1983 | European Pat. Off. ............. 424/76 |
| 44-20360 | 9/1969 | Japan ................................... 514/783 |

OTHER PUBLICATIONS

Steinmetz, 1957, Codex Vegetabilis, 404.
U.S. Dispensatory, 12/1926, 21st edition, p. 1284.
Derwent Abstract of Japanese Patent No. 7214901-R, Abstract #30662T-4/8/69, Ono.

Primary Examiner—Dale R. Ore
Attorney, Agent, or Firm—Wenderoth, Lind & Ponack

[57] ABSTRACT

Deodorant compositions containing, as an active ingredient, juice which is pressed out from fruits of Ebenaceae plants, a method of preparing such active ingredient and the use of such compositions as a deodorant in various environmental conditions.

7 Claims, No Drawings

DEODORANT COMPOSITIONS CONTAINING PERSIMMON JUICE AS ACTIVE INGREDIENT

BACKGROUND OF THE INVENTION (a) Field of the Invention

This invention relates to deodorant compositions containing, as a main component, persimmon juice. More particularly, this invention relates to use of pressed juice of persimmon fruits, in combination with conventional excipients, adjuvants and additives, for removing undesirable odors from various enviromental conditions.

(b) Description of the Prior Art

A persimmon tree is a plant of Ebenaceae which grows or is cultivated in the tropic and temperate zones of the world including Japan and China. It is said that Ebenaceae plants are classified into seven genuses and 20 species and fruits of some kinds of persimmon trees contain, even after their maturity, persimmon tannine. The persimmon tannine is known to be available for some medicines, mordanting and leather-tanning agents.

One of the present inventors and his co-workers formerly found that dry-distllates from leaves of theaceae plants had a potent and long acting effect for deodorization, and they filed for a patent on such deodorant compositions as containing the dry-distillates as an active ingredient, one of which was already published as European Patent Publication No. 0077 047 B1.

This invention has been identified by the present inventors to be more potent in its deodorant effect than the dry-distillates of theaceae leaves.

It is believed by the present inventors that no one has disclosed the deodorant effect of pressed juice obtained from persimmon fruits.

DETAILED DESCRIPTION OF THE INVENTION

In this invention, raw persimmon fruits, either sweet or astringent ones but preferably immature ones, are available as a starting material and they are pressed by an ordinary pressing machine to obtain juice, which is made into powders under a reduced pressure or the thus obtained pressed juice is preserved in a closed vessel for about half a year with or without enzyme, then the resultant sugars are removed by filtration or dialysis and the residue is dried under a reduced pressure to obtain powders.

EXAMPLES

The present invention will be more fully understood with reference to the following embodiments:

Example 1

Ten kilograms of immature fruits of persimmon (Diospyros Kaki) was pressed by an ordinary pressing machine to obtain 5 Kg of pressed juice, which was dried at a reduced pressure, which gave 600 g of powders.

Example 2

One kilogram of immature fruits of persimmon (Diospyros Lotus) was pressed out by an ordinary pressing machine to obtain 500 g of juice. The thus obtained juice was preserved in a closed vessel for six months to cause self-fermentation, then the resultant sugars were removed by dialysis and the residue was dried at a reduced presssure, which gave 400 g of powders.

Examples of a deodorant effect of the active ingredient of this invention are indicated by following experiments:

Experiment 1

Sense of Smell test

[Method]

To a solution in which 0.1 g of garlic extracts were dissolved in 100 ml of water, 1 ml and 2 ml of 10% aqueous solution of the active ingredient obtained from above Example 1 were added separately. With these test solutions, six members of a panel recorded their degree of perception to garlic ordors in the following order;

0—Not pereceptible
1—Little perceptible
2—Narrowly perceptible of what kind of orders
3—Perceptible
4—Perceptible of strong order
5—Perceptible of very strong order

[Result]

TABLE 1

| Panel member No. | Solution (1 ml added) | Solution (2 ml added) | Solution (Not added) |
|---|---|---|---|
| I | 2 | 0 | 5 |
| II | 3 | 1 | 5 |
| III | 2 | 0 | 4 |
| IV | 1 | 0 | 4 |
| V | 2 | 0 | 4 |
| VI | 2 | 1 | 4 |

Experiment 2

[Test solution]

Solution A; 2 w/w % aqueous solution of the active ingredient prepared in Example 1.

Solution B; 5 w/w % propylene glycol solution of the dry-distillates obtained from theaceae leaves referred to previously.

(a) Ammonia

Into each closed 500 ml vessed which contained a fixed concentration of 28% ammonia, 1 ml each of Solution A and Solution B was added separately at room temperature. 10 minutes after the addition, the free ammonia gas was taken out from the vessel. A removing percentage was calculated on the basis of the determined value of each remaining concentration of the ammonia.

[Result]

TABLE 2

| Test Solu. | Concentr. at Beginning (ppm) | Concentr. after 10 min. (ppm) | Removing Rate (%) |
|---|---|---|---|
| A | 11,000 | 3330 | 69.8 |
| B | 11,000 | 5560 | 48.7 |

(b) Trimethylamine

In the same manner as with above experiment (a), but substituting ammonia for trimethylamine, the following result was observed, wherein the determination of trimethylamine was carried out by gas chromatography.

TABLE 3

| Test Solu. | Concentr. at Beginning (ppm) | Concentr. after 10 min. (ppm) | Removing Rate (%) |
|---|---|---|---|
| A | 6800 | 81 | 98.8 |

TABLE 3-continued

| Test Solu. | Concentr. at Beginning (ppm) | Concentr. after 10 min. (ppm) | Removing Rate (%) |
|---|---|---|---|
| B | 6800 | 970 | 85.8 |

(c) Acetic acid

The volume of each test solution, diluted ten times, required to completely react with a fixed quantity of acetic acid was determined separately by a titration method.

It required 4 ml with Test solution A and 17 with Test solution B. Consequently, the ability of Test solution B for complete reaction with acetic acid was equivalent to $4/17 \times 100 = 23.5\%$ of that of Test solution A.

(d) Hydrogen sulfide

In the same manner as with experiment (a) but substituting ammonia for hydrogen sulfide, the following result was observed, wherein the concentration of hydrogen sulfide was determined using an inspection tube for hydrogen sulfide.

[Result]

TABLE 4

| Test Solu. | Concentr. at Beginning (ppm) | Concentr. after 10 min. (ppm) | Removing Rate (%) |
|---|---|---|---|
| A | 10 | 5 | 50 |
| B | 10 | 5 | 50 |

The constituents of the active ingredient of this invention have not been definitely clarified. However, they are presumed to consist of flavanols, flavonols and other organic higher molecules. Their deodorant effectiveness may be due to a complex mechanism consisting of clathrating, addition and neutralization reactions of the active ingredient with malodorous sources in addition to biological reactions in human beings, such as inhibition of olfactory receptors.

The active ingredient of this invention can be formulated for deodorant uses in various forms with the aid of excipients, adjuvants and additives known in the art, depending on location and purpose of application, some of which are illustrated as follows:

Fumigation preparations:

| The active ingredient | 0.5 parts(w) |
|---|---|
| Powdered charcoal | 60 parts(w) |
| Carboxymethylcellulose | 1.0 part (w) |
| Powdered perfume | 9.0 parts(w) |

The above components are kneaded with hot water and molded into sticks and dried.

Aerosol preparations:

| The active ingredient | 0.2 parts(w) |
|---|---|
| Dimethylether | 110 parts(w) |
| Refined water | 108 parts(w) |
| Perfume | optional |

The above components are filled into aerosol cans by a conventional method.

Granule preparations:

| The active ingredient | 1 part(w) |
|---|---|
| Lactose | 75 parts(w) |
| Dextrin | 24 parts(w) |

The above ingredient are kneaded with water, then molded by a conventional method.

Moreover, the active ingredient of this invention can be formulated for practical uses by being absorbed into porous unglazed plates or by soaking into papers, fibres and synthetic resins.

The thus produced variety of preparations is useful for deodorization in various enviromental places and conditions and can be used in, for example, refrigerators, shoes, medicines and cosmetics including an underarm deodorant and an anti-halitosis agent. It is especially useful in dealing with faeces and urine in hospitals and aged people's homes.

An effective dose of the active ingredient of this invention depends, of course, upon the amount and kind of malodorous sources. However, it is tentatively recommended to employ 0.01 to 1% by weight of the ingredient to a given weight of malodorous substances.

What we claim is:

1. A deodorant composition comprising as an active deodorant ingredient an effective deodorizing amount of persimmon juice which is pressed out from persimmon fruits and an excipient or adjuvant therefor selected from the group consisting of fumigants, aerosols, fibers, paper, granules and synthetic resins.

2. A composition in accordance with claim 1, wherein said fruit is immature fruit.

3. A composition in accordance with claim 1, wherein said juice is in powder form.

4. A process for preparing a deodorizing agent, which comprises pressing juice out from fruit of a persimmon, storing the juice in a closed vessel for about six months, removing resultant sugars from the juice, and drying the remaining juice residue at reduced pressure to form solid powder.

5. A method of deodorizing a malodorous environmental locus, which comprises introducing into said locus a deodorizing amount of juice pressed out from fruit of a persimmon.

6. A method in accordance with claim 5, wherein said fruit is immature fruit.

7. A method in accordance with claim 5, wherein said juice is in powder form.

* * * * *